United States Patent [19]
Dillard et al.

[11] Patent Number: 4,991,452
[45] Date of Patent: Feb. 12, 1991

[54] SAMPLER FOR HAZARDOUS SOLID MATERIALS

[75] Inventors: Ralph H. Dillard; Arthur H. Reppert, Jr.; Isaac B. Wilson, Jr., all of Richmond, Va.

[73] Assignee: E. I. Du Pont de Nemours and Company, Wilmington, Del.

[21] Appl. No.: 479,876

[22] Filed: Feb. 14, 1990

[51] Int. Cl.$^5$ ............................................. G01N 1/08
[52] U.S. Cl. .................................................. 73/864.44
[58] Field of Search ........... 73/864.41, 864.43–864.45, 73/864.34; 83/919; 175/58, 403, 404; 408/204

[56] References Cited
U.S. PATENT DOCUMENTS

| | | | |
|---|---|---|---|
| 3,843,198 | 10/1974 | Reynolds | 73/864.41 |
| 4,754,655 | 7/1988 | Parker, III et al. | 73/864.44 |
| 4,887,413 | 12/1989 | Tuckey, Jr. | 73/864.44 |

*Primary Examiner*—Robert Raevis

[57] ABSTRACT

Apparatus for sampling potentially hazardous solid materials is provided. The apparatus includes sampler head mounted on a handle having an interior bore with a connector for connecting the interior bore to a source of vacuum. The sampler head of the apparatus of the invention includes a collector having a funnel-shaped wall which diverges away from the handle from a minor opening to a major opening. A separator plate is provided having an exterior surface oriented in the direction of divergence of the funnel-shaped wall and with an interior surface in communication with the interior bore of the handle. A cutter holder is mounted on the separator plate and extends into the collector with the cutter holder being generally centered with respect to the minor opening of the collector and the funnel-shaped wall. The apparatus further includes an elongate, removable cutter sleeve which is attachable at an attachment end to the cutter holder. The cutter sleeve has a cutting end sharpened to cut and receive a sample into the interior of the cutter sleeve when attached to the cutter holder with the cutter sleeve having a wall thickness not greater than about 0.1 inch. The minor opening of the collector and the cutter holder each are dimensioned such that an annular area of the exterior surface of the separator plate about the cutter holder is exposed to the interior of the collector and has a minimum dimension sufficient to permit access for easy cleaning. At least one aperture is formed in the exposed annular area of the separator plate to communicate vacuum supplied to the bore in the handle to the collector.

7 Claims, 3 Drawing Sheets

SAMPLER FOR HAZARDOUS SOLID MATERIALS

BACKGROUND OF THE INVENTION

The present invention relates to apparatus for sampling hazardous materials and more particularly relates to apparatus for the sampling of solid hazardous materials safely with minimal release of hazardous particulates.

Exposure of the lungs to asbestos is known to causes diseases including asbestosis, lung cancer, and mesothelioma. Unfortunately, before the connection between these diseases and asbestos was known, asbestos was used widely in construction materials and insulation for many years and its presence in buildings and private residences is a potential hazard. Applicable government standards now reflect the perceived risk from asbestos exposure. Accordingly, it is frequently necessary to sample solid materials suspected of containing asbestos to detect its presence so that exposure to such materials can be appropriately controlled.

While various apparatus for sampling solid materials are known, such apparatus have not always been suitable for the sampling of friable materials containing asbestos. One type of sampler is simply a sharpened tube with a handle which is capable of cutting a core of a solid material. However, the use of such apparatus can expose the user of the tool and others in the area to airborne particulates which are released during the sampling process. Another apparatus is disclosed in U.S. Pat. No. 4,754,655 which can greatly curtail the release of particulates since it is connected to a high efficiency particulate air (HEPA) vacuum device. In this tool, a sample canister is provided within a handle and a tubular coring member is used to cut a sample to be deposited inside the sample canister. A conical shroud is provided about the coring member and is supplied with vacuum from the HEPA vacuum cleaner to catch any particulates which are released.

The sampling apparatus disclosed in U.S. Pat. No. 4,754,655, however, has several disadvantages. Because the coring member must be large enough to accommodate the sample cannister, it is large in diameter and has thick walls which make it difficult to penetrate far enough into the material to obtain a representative sample. With a tool of this type, it is especially difficult to sample "hard-style" asbestos containing insulation such as that used for pipe or vessel coverings. Moreover, the tool must be disassembled to remove the sample bottle which can then expose the user to asbestos or other hazardous material. This tool also has tight crevices which are difficult to clean and thus can cause accidental exposure to the hazardous material while the tool is being stored or being handled by the user when respiratory and other protective devices are not being worn.

SUMMARY OF THE INVENTION

In accordance with the invention, apparatus for sampling potentially hazardous solid materials is provided. The apparatus includes a handle having an interior bore with a connector for connecting the interior bore to a source of vacuum. A sampler head is mounted on the handle for sampling the material suspected to be hazardous.

The sampler head of the apparatus of the invention includes a collector having a funnel-shaped wall which diverges away from the handle from a minor opening to a major opening. A separator plate is provided having an exterior surface oriented in the direction of divergence of the funnel-shaped wall and having an interior surface in communication with the interior bore of the handle. A cutter holder is mounted on the separator plate and extends into the collector with the cutter holder being generally centered with respect to the minor opening of the collector and the funnel-shaped wall. The apparatus further includes an elongate, removable cutter sleeve which is attachable at an attachment end to the cutter holder. The cutter sleeve has a cutting end sharpened to cut and receive a sample into the interior of the cutter sleeve when attached to the cutter holder with the cutter sleeve having a wall thickness not greater than about 0.1 inch. The minor opening of the collector and the cutter holder each are dimensioned such that an annular area of the exterior surface of the separator plate about the cutter holder is exposed to the interior of the collector and has a minimum dimension sufficient to permit access for easy cleaning. At least one aperture is formed in the exposed annular area of the separator plate to communicate vacuum supplied to the bore in the handle to the collector.

In accordance with a preferred form of the invention, the separator plate of the sampling apparatus has an exposed annular area about the cutter holder which has a minimum dimension of not less than about 0.5 inch. In another preferred form of the invention, the separator plate is generally planer and is generally perpendicular to the cutter holder and the cutter sleeve.

BRIEF DESCRIPTION OF THE DRAWINGS

The present invention may best be understood by reference to following Detailed Description and accompanying drawings in which.

DETAILED DESCRIPTION

Figure 1:
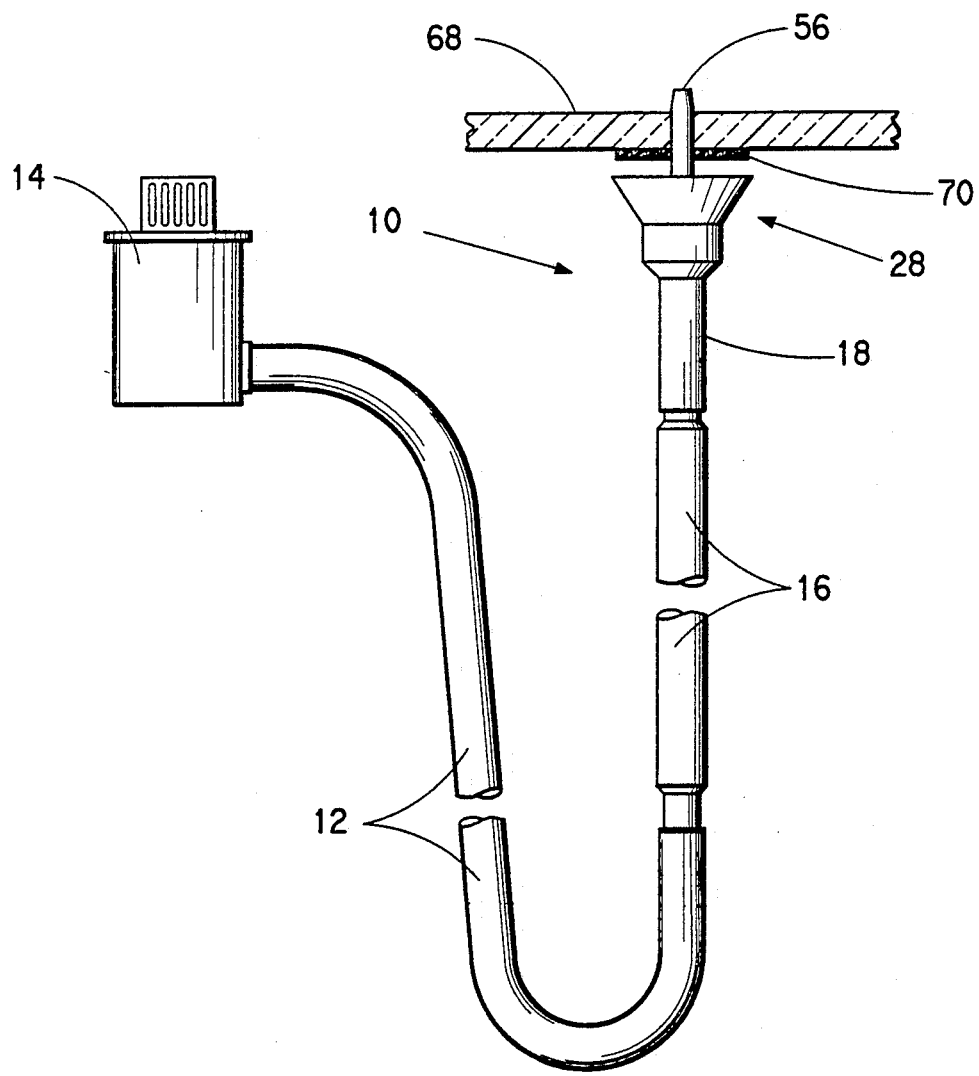
FIG. 1 is a partially diagrammatical elevational view of a preferred sampling apparatus in accordance with the present invention connected to a vacuum device.

Referring to the drawings in which like reference characters designate like or corresponding parts, FIG. 1 illustrates a preferred apparatus 10 for taking samples of solid hazardous materials such as those suspected of containing asbestos. The apparatus 10 is shown attached to a hose 12 which is connected at its other end to a vacuum device 14. Hose 12 includes an extension tube 16 adjacent the apparatus 10 to facilitate handling and to reach overhead locations. A suitable high efficiency particulate air (HEPA) filter device (not shown) is installed on the output of the vacuum device 14 to prevent fine particulates which are drawn into the apparatus from being released. (The vacuum device 14 and the HEPA filter are referred to hereinafter as HEPA vacuum device 14.)

Figure 2:
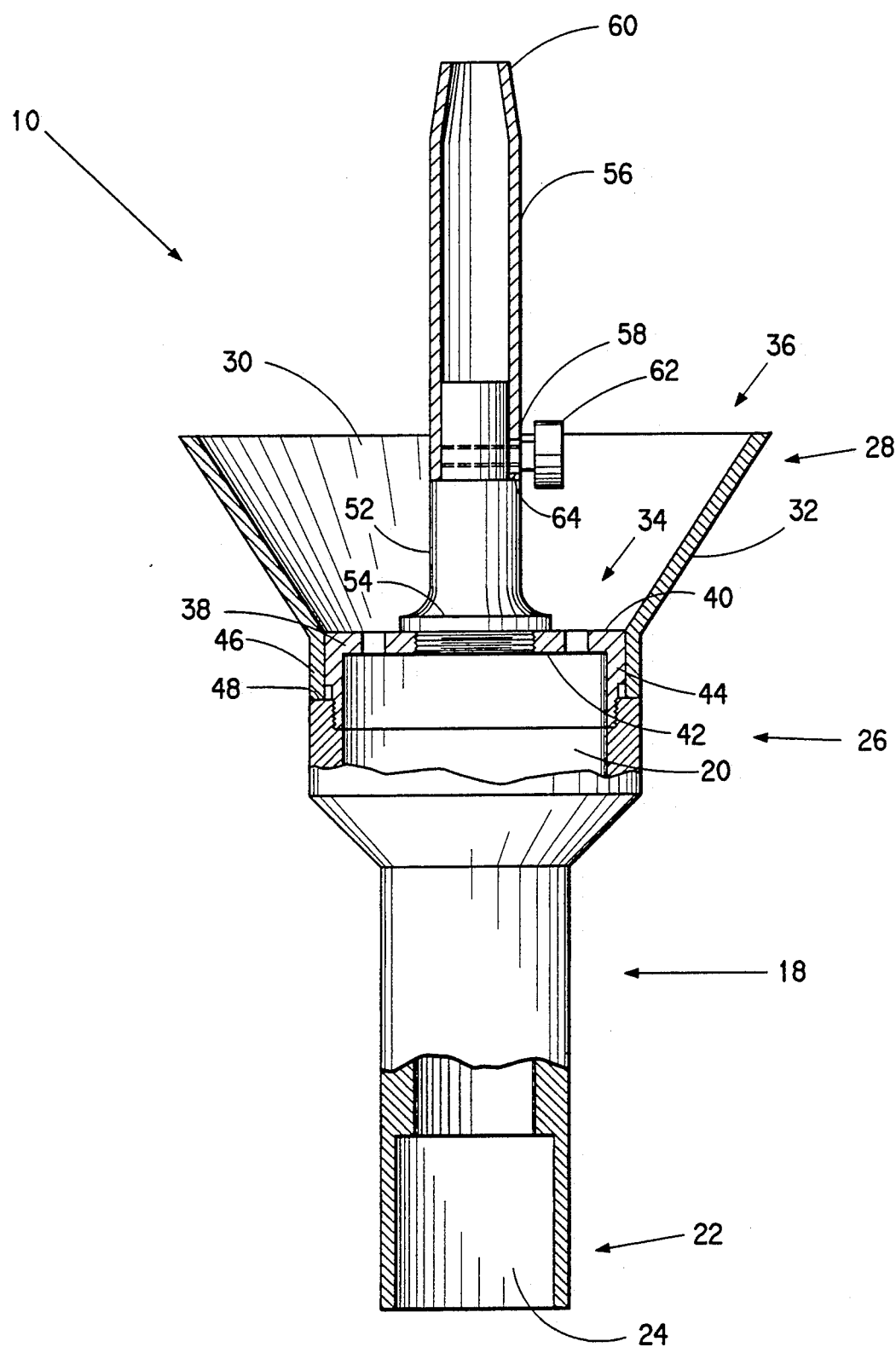
FIG. 2 is a partially cross-sectional, elevational view of the sampling apparatus of the present invention.

Referring now primarily to FIG. 2, the sampling apparatus 10 comprises a tubular handle 18 with an interior bore 20. The bottom end 22 of the handle 18 provides a connector bore 24 which is dimensioned to slidably receive the upper end of the extension tube 16. The upper end 26 of the handle 18 has an enlarged diameter providing an enlarged upper area of the bore 20 to accommodate attachment to a suitably dimensioned sampler head 28 as will become more apparent hereinafter.

The sampler head 28 is mounted on the enlarged upper end 26 of the handle 18. The sampler head 28 includes a collector 30 having a funnel-shaped wall 32 which diverges away from the handle 18 from a minor opening 34 to a major opening 36. In the embodiment depicted the funnel-shaped wall 32 is conical in shape with its axis being coaxial to the axis of the tubular handle 18.

The sampler head 28 also includes a separator plate 38 having an exterior surface 40 oriented in the direction of divergence of the funnel-shaped wall 32 and with an interior surface 42 in communication with the interior bore 20 of the handle 18. In the embodiment depicted, the separator plate 38 is attached to the handle by means of a downwardly-extending tubular extension 44 joined to periphery of the the interior surface 42. The tubular extension has a partially-threaded cylindrical exterior which is threadably received into the bore 20 at the enlarged upper end 26 of the handle 18. The tubular portion is only partially inserted in the bore 20 so that an unthreaded portion of the tubular extension 44 extends upwardly past the end 26 of the handle 20. A mounting sleeve 46 of the collector 30 extends from the minor opening 34 of the collector and is secured on the tubular extension 44 of separator plate 38 such as by friction fitting. In the embodiment depicted, the end 26 of the handle 18 forms an abutting annular shoulder 48 which limits insertion of the mounting sleeve 46 so that the minor opening 34 of the collector 30 is aligned with the exterior surface of the separator plate 38 and so that no crevice is formed at the transition between the wall 32 and the separator plate 38. Also in the preferred embodiment depicted, the exterior surface 40 of the separator plate 38 is planer and is generally perpendicular to the axis of the tubular handle 18.

Figure 3:
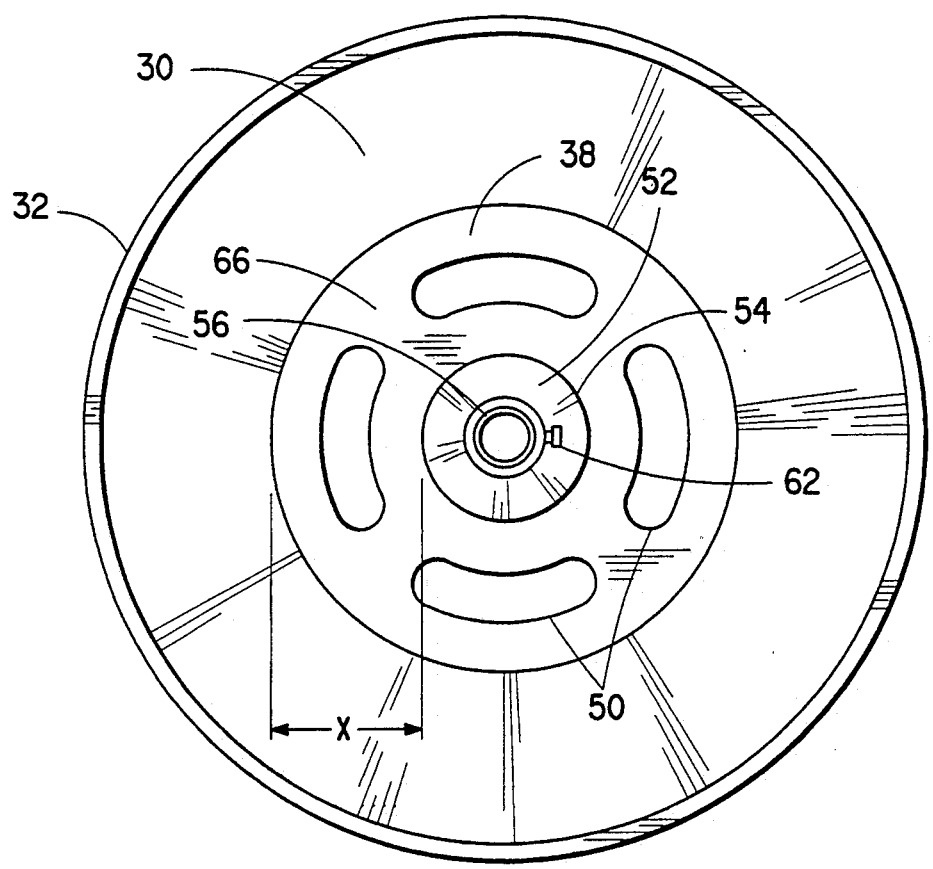
FIG. 3 is an enlarged top view of the apparatus of the invention.

As will be more apparent hereinafter, at least one aperture 50, and preferably several spaced-apart apertures in a circular arrangement as shown in FIG. 3, are formed in the separator plate 38 to communicate vacuum supplied to the bore 20 of the handle 18 to the collector 30.

A cutter holder 52 is mounted on the separator plate 38 and extends into the collector 30 with the cutter holder 52 being generally centered with respect to the minor opening 34 of the collector and the funnel-shaped wall 32. Preferably, the cutter holder 52 is generally cylindrical in shape and is perpendicular to the exterior surface of the separator plate. The cutter holder can be mounted as shown with mounting base 54 threadably inserted into a central bore in the separator plate 38. In the preferred embodiment depicted, the cutter holder has a length such that it terminates adjacent the major opening 36 of the collector 30.

The sampling head 28 of the apparatus 10 further includes an elongate, preferably cylindrical cutter sleeve 56 which is attachable at an attachment end 58 to the cutter holder 52 as will be explained hereinafter. The cutter sleeve 56 has a cutting end 60 sharpened to cut and receive a sample into the interior of the cutter sleeve when the cutter sleeve is attached to the cutter holder 52. To facilitate cutting, the cutter sleeve has a wall thickness which is not greater than about 0.1 inch, preferably 0.06 inch or less provided that it is fabricated from a suitably strong material to accomplish cutting. The cutter sleeve 56 preferably has a length such that is extends past the major opening 36 of the collector by between about 2 and about 6 inches, depending upon the thickness of the material to be sampled.

In the preferred form of the invention, the cutter sleeve 56 is attached to the cutter holder 52 by a portion of the cutter holder 52 being adapted to be received into the attachment end 58 of the cutter sleeve 56. In the embodiment depicted, this is accomplished by the end of the cutter holder 52 being reduced in diameter as shown. A shoulder screw 62 is threadably received into the reduced diameter portion of the cutter holder 52. In addition, a longitudinally-aligned slot 64 (with respect to the length of the cutter sleeve) extends into the attachment end 58 of the cutter sleeve 56 for receiving the shoulder screw when the reduced diameter portion of the cutter holder is received into the cutter sleeve. The shoulder screw 62 is tightened to attach the cutter sleeve 56 to the reduced diameter portion of the cutter holder 52.

As best shown in FIG. 3, the diameter of the minor opening 34 of the collector 30 and the diameter of the cutter holder 52 each are dimensioned such that an exposed annular area 66 of the exterior surface 40 of the separator plate 38 about the cutter holder 52 is exposed to the interior of the collector 30 and has a minimum dimension sufficient to permit access for easy cleaning. Preferably, the exposed annular area has a minimum dimension (identified by x in FIG. 3) which is not less than about 0.5 inch.

In use, the connector bore 24 in the handle 18 of the apparatus is placed on the extension handle 16 of the hose 12 and the HEPA vacuum device 14 is turned on. The area of the solid material 68 to be sampled is moistened thoroughly with water and a wet sponge 70 is placed over the area to minimize the release of particulates. The cutting edge of the cutter sleeve 56 is placed in contact with the sponge 70 over the area to be sampled and the handle 18 is pressed upwardly to cause the cutter sleeve 56 to penetrate the sponge 70 and the material 68 and the sample of the hazardous material is received into the interior of the cutter sleeve with a section of the sponge closing off the attachment end 58 of the cutter sleeve 56. Substantially all fibrous debris and particulate material released into the air by the disturbance of the solid material is pulled through the air space between the material surface and the collector 30, through the apertures 50 in the separator plate 38, along the bore 20 so that it is captured in the HEPA vacuum device 14.

With the HEPA vacuum device 14 still running, the cutter sleeve 56 is removed from the solid material 68 and a suitably dimensioned container (plastic bag or sample vial) is placed over the cutter sleeve and the shoulder screw is loosened to release the cutter sleeve 56 containing the sample into the container. Since a section of the sponge is in the attachment end 58 of the cutter sleeve 56, there is less risk of release of particulates as the cutter sleeve is removed from the apparatus. No other disassembly of the preferred apparatus is needed to remove the sample. The container with the sample and cutter sleeve 56 sealed inside may be safely transported to a convenient location for analysis.

The apparatus of the invention provides a means by which samples of hazardous materials, such as friable materials containing asbestos, can be taken safely since the airborne particulates are caught and filtered from the air as the sample is taken. The hazard of the materials to the investigator and building occupants is thereby reduced substantially. In addition, due to the thinwalled cutter sleeve, the apparatus of the invention is capable of efficiently sampling thick, difficult to penetrate materials and is particularly well-suited for sampling hard-style asbestos containing insulation.

The inside of the collector 30 can be cleaned easily such as by wiping with a suitable disposable cloth since the exposed portion of the separator plate 38 has a width sufficient to facilitate access and there are no deep crevices in the preferred embodiment in which hazardous material may become entrapped. Cleaning can be performed particularly safely if done while the HEPA vacuum device 14 is running which will cause substantially all debris in the collector 30 to be drawn into the HEPA filter by the vacuum device.

While a preferred embodiment has been shown and described in the foregoing detailed description, it will be understood that the invention is capable of numerous modifications, rearrangements and substitution of parts without departing from the spirit of the invention as set forth in the appended claims.

We claim:

1. Apparatus for sampling potentially hazardous solid materials comprising:
    a handle having an interior bore, said handle having connection means for connecting said interior bore to a source of vacuum; and
    sampler means mounted on said handle for sampling said material, said sampler means comprising:
    a collector having a funnel-shaped wall which diverges away from said handle from a minor opening to a major opening,
    a separator plate having an exterior surface oriented in the direction of divergence of said funnel-shaped wall and with an interior surface in communication with said interior bore of said handle;
    a cutter holder mounted in said separator plate and extending into said collector, said cutter holder being generally centered with respect to said minor opening of said collector and said funnel-shaped wall;
    an elongate, removable cutter sleeve and means for attaching an attachment end of said cutter sleeve to said cutter holder, said cutter sleeve having a cutting end sharpened to cut and receive a sample into the interior of said cutter sleeve when attached to said cutter holder, said cutter sleeve having a wall thickness not greater than about 0.1 inch;
    said minor opening of said collector and said cutter holder each being dimensioned such that an annular area of said exterior surface of said separator plate about said cutter holder is exposed to the interior of said collector and has a minimum dimension between said cutter holder and said funnel-shaped wall sufficient to permit access for easy cleaning; and
    at least one aperture in said exposed annular area of said separator plate to communicate vacuum supplied to said bore in said handle to said collector.

2. The apparatus of claim 1 wherein said exposed annular area has a minimum dimension which is not less than about 0.5 inch.

3. The apparatus of claim 1 wherein said exterior surface of said separator plate is generally planar and is generally perpendicular to said cutter holder and said cutter sleeve.

4. The apparatus of claim 3 wherein said funnel-shaped wall is conical in shape with its axis being generally coaxial with said cutter holder and cutter sleeve.

5. The apparatus of claim 1 wherein said cutter sleeve comprises an open-ended cylindrical tube having an outside diameter of not greater than 1.0 inch.

6. The apparatus of claim 5 wherein said means for attaching said cutter sleeve to said cutter holder comprises:
    a portion of said cutter holder adapted to be received into the attachment end of said cutter sleeve;
    a shoulder screw threadably received into said portion of said cutter holder; and
    a longitudinally-aligned slot extending into said attachment end of said cutter sleeve for receiving said shoulder screw when said portion of said cutter holder is received into said cutter sleeve.

7. The apparatus of claim 1 wherein said cutter holder terminates proximate to said major opening of said collector.

* * * * *